United States Patent
Choi et al.

(10) Patent No.: US 10,702,626 B2
(45) Date of Patent: Jul. 7, 2020

(54) METHOD FOR PREPARING SUPERABSORBENT POLYMER AND SUPERABSORBENT POLYMER

(71) Applicants: LG Chem, Ltd., Seoul (KR); Seoul National University R&DB Foundation, Seoul (KR)

(72) Inventors: Yong Seok Choi, Daejeon (KR); Young Sam Kim, Daejeon (KR); Jong Doo Lim, Daejeon (KR); Jong-Chan Lee, Seoul (KR); Na Kyung Kim, Seoul (KR); Jinseok Kim, Incheon (KR)

(73) Assignees: LG Chem. Ltd. (KR); Seoul National University R&DB Foundation (KR)

( * ) Notice: Subject to any disclaimer, the term of this patent is extended or adjusted under 35 U.S.C. 154(b) by 0 days.

(21) Appl. No.: 16/077,338

(22) PCT Filed: Nov. 27, 2017

(86) PCT No.: PCT/KR2017/013612
§ 371 (c)(1),
(2) Date: Aug. 10, 2018

(87) PCT Pub. No.: WO2018/117452
PCT Pub. Date: Jun. 28, 2018

(65) Prior Publication Data
US 2019/0046682 A1    Feb. 14, 2019

(30) Foreign Application Priority Data

Dec. 22, 2016 (KR) .......................... 10-2016-0177067
Dec. 22, 2016 (KR) .......................... 10-2016-0177068

(51) Int. Cl.
*A61L 15/60* (2006.01)
*C08F 2/44* (2006.01)
(Continued)

(52) U.S. Cl.
CPC ............ *A61L 15/60* (2013.01); *A61L 15/18* (2013.01); *A61L 15/26* (2013.01); *A61L 15/44* (2013.01);
(Continued)

(58) Field of Classification Search
CPC .......... A61L 15/60; A61L 15/46; A61L 15/26; A61L 15/18; A61L 2300/404;
(Continued)

(56) References Cited

U.S. PATENT DOCUMENTS 5,961,843 A    10/1999   Hayakawa et al.
6,306,795 B1 * 10/2001   Ryan ..................... B01J 23/72
                                                     423/604
(Continued)

FOREIGN PATENT DOCUMENTS

EP    0200433 A2    11/1986
EP    3056521 A1    8/2016
(Continued)

OTHER PUBLICATIONS

Extended European Search Report and Written Opinion for EP Application No. 17883009.7, dated Jan. 25, 2019.
(Continued)

*Primary Examiner* — Andrew J. Oyer
(74) *Attorney, Agent, or Firm* — Lerner, David, Littenberg, Krumholz & Mentlik, LLP

(57) ABSTRACT

The present invention relates to a method for preparing superabsorbent polymer that has antibacterial activity, in which the basic properties of superabsorbent polymer are maintained or improved, and may exhibits excellent bacterial proliferation inhibition effect, and superabsorbent polymer prepared thereby. The preparation method of superabsorbent polymer comprises the steps of: forming base polymer powder using hydogel polymer comprising cross-
(Continued)

linked polymer, and then, surface crosslinking the base polymer powder using a surface crosslinking solution comprising a surface crosslinking agent and cuprous oxide, wherein the cuprous oxide is included in the content of 0.001 to 2.5 parts by weight, based on 100 parts by weight of the base polymer powder.

15 Claims, 2 Drawing Sheets

(51) Int. Cl.
| | |
|---|---|
| C08J 3/24 | (2006.01) |
| C08J 3/12 | (2006.01) |
| C08J 3/075 | (2006.01) |
| C08F 2/10 | (2006.01) |
| A61L 15/46 | (2006.01) |
| C08F 2/48 | (2006.01) |
| C08K 3/22 | (2006.01) |
| A61L 15/18 | (2006.01) |
| A61L 15/26 | (2006.01) |
| A61L 15/44 | (2006.01) |
| B01J 20/06 | (2006.01) |
| B01J 20/26 | (2006.01) |
| B01J 20/28 | (2006.01) |
| B01J 20/30 | (2006.01) |
| A61L 15/42 | (2006.01) |

(52) U.S. Cl.
CPC .............. *A61L 15/46* (2013.01); *B01J 20/06* (2013.01); *B01J 20/267* (2013.01); *B01J 20/28016* (2013.01); *B01J 20/3021* (2013.01); *B01J 20/3085* (2013.01); *C08F 2/10* (2013.01); *C08F 2/44* (2013.01); *C08F 2/48* (2013.01); *C08J 3/075* (2013.01); *C08J 3/12* (2013.01); *C08J 3/24* (2013.01); *C08J 3/245* (2013.01); *A61L 15/425* (2013.01); *A61L 2300/102* (2013.01); *A61L 2300/404* (2013.01); *C08J 2333/02* (2013.01); *C08K 2003/2248* (2013.01)

(58) Field of Classification Search
CPC .. A61L 2300/102; A61L 15/425; A61L 15/44; C08F 2/48; C08F 2/10; C08F 2/44; B01J 20/28016; B01J 20/267; B01J 20/06; B01J 20/3021; C08J 2333/02; C08J 3/245; C08J 3/075; C08J 3/12; C08J 3/24; C08K 2003/2248

See application file for complete search history.

(56) References Cited

U.S. PATENT DOCUMENTS

| | | | |
|---|---|---|---|
| 2008/0063693 | A1 | 3/2008 | Cook et al. |
| 2008/0221277 | A1* | 9/2008 | Walden .................. A61L 15/18 |
| | | | 525/418 |
| 2010/0247615 | A1 | 9/2010 | Toreki et al. |
| 2013/0195841 | A1 | 8/2013 | Gabbay |
| 2014/0221948 | A1 | 8/2014 | Riesinger |
| 2014/0312273 | A1 | 10/2014 | Wattebled et al. |
| 2015/0320035 | A1 | 11/2015 | Trinder, II et al. |
| 2017/0216815 | A1 | 8/2017 | Jang et al. |
| 2018/0289854 | A1* | 10/2018 | Varona ................. B01J 20/3085 |

FOREIGN PATENT DOCUMENTS

| | | |
|---|---|---|
| EP | 3406638 A1 | 11/2018 |
| EP | 3409712 A1 | 12/2018 |
| JP | 2003335864 | 11/2003 |
| JP | 2008536989 A | 9/2008 |
| JP | 4401044 B2 | 1/2010 |
| JP | 2012518062 A | 8/2012 |
| KR | 100918807 B1 | 9/2009 |
| KR | 20130045836 A | 5/2013 |
| KR | 20150083829 A | 7/2015 |
| KR | 20170009546 A | 1/2017 |
| WO | 03002164 A2 | 1/2003 |
| WO | 2010029074 A2 | 3/2010 |

OTHER PUBLICATIONS

Odian, G, "Principles of Polymerization," 2nd Edition, copyright 1981, John Wiley & Sons, Inc. ISBN 0-471-05146-2, p. 203.
Schwaim, R., "UV Coatings: Baiscs, Recents Developments and New Applications," Elsevier Science, Dec. 21, 2006, ISBN-10: 0444529799; ISBN-13: 978-0444529794, p. 115.
International Search Report for PCT/KR2017/013612 dated Apr. 16, 2018.

* cited by examiner

[FIG. 1]
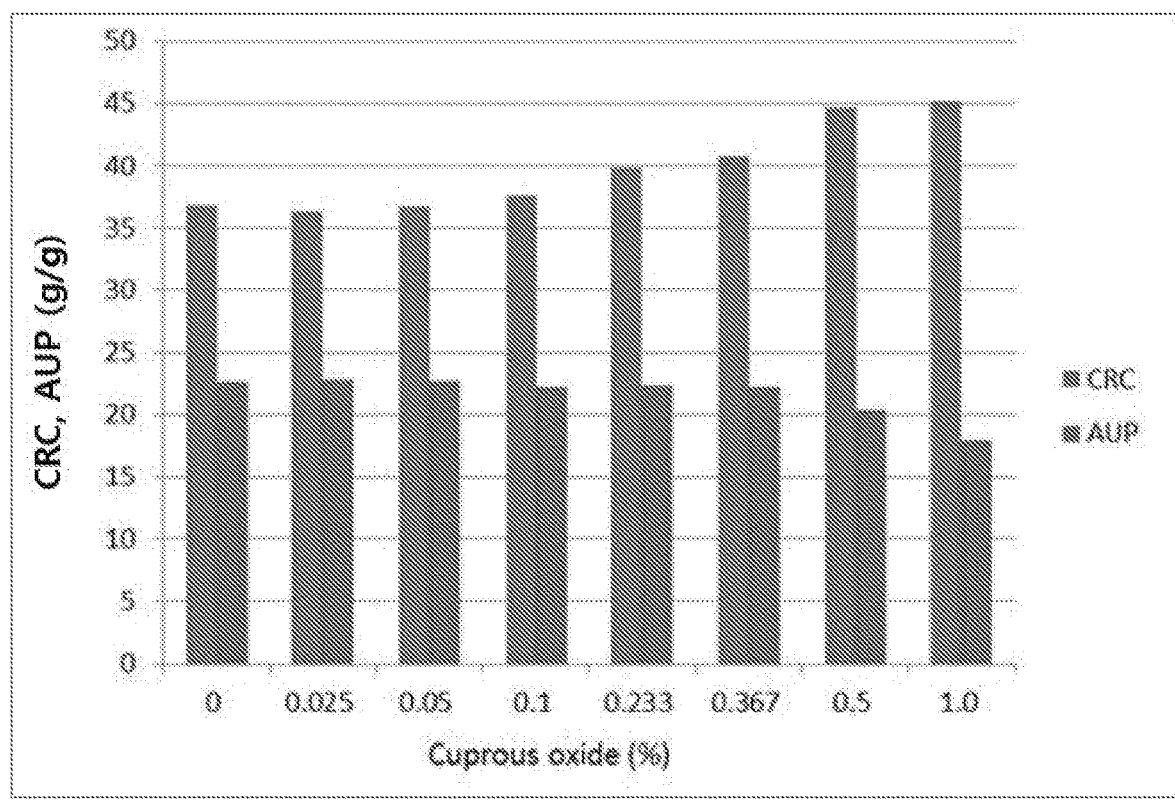

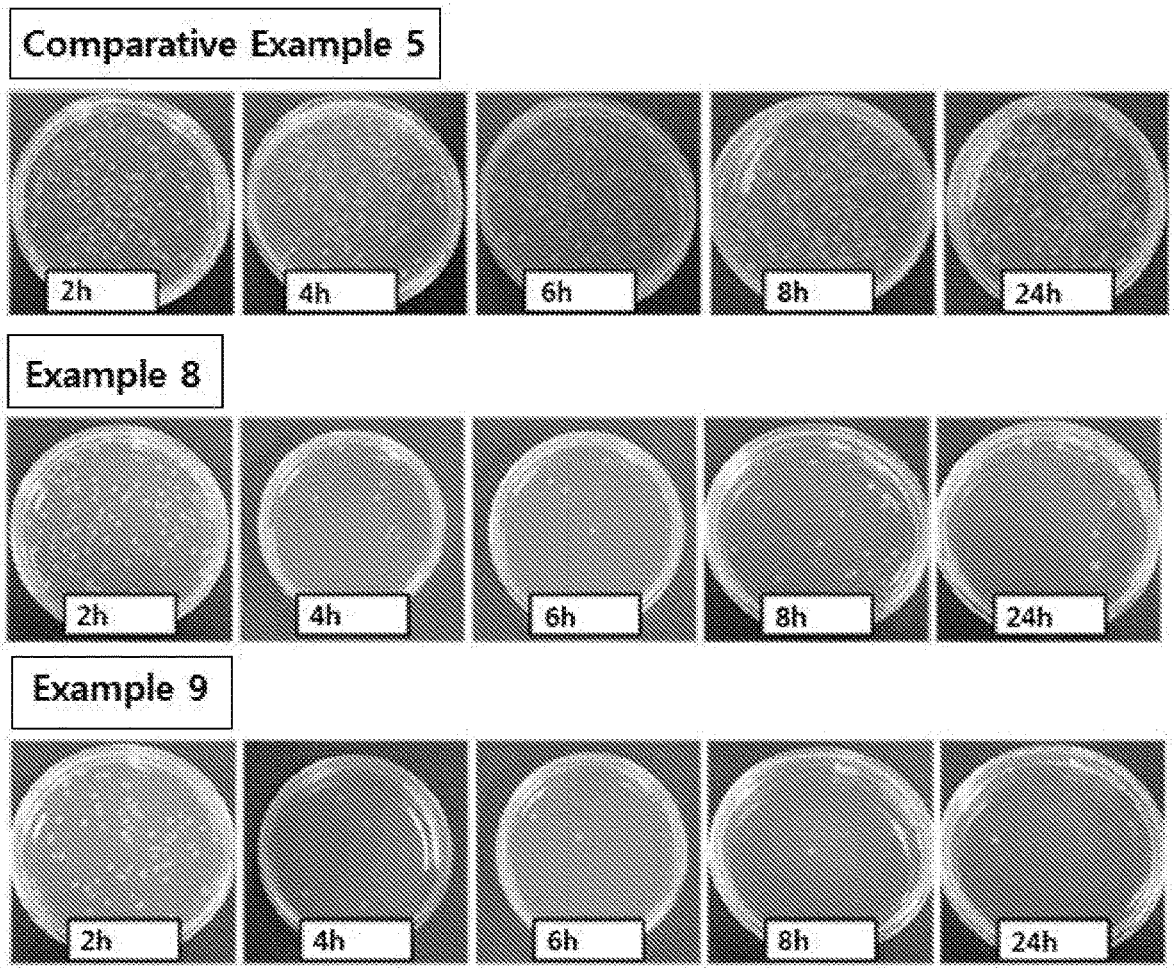
[FIG. 2]

METHOD FOR PREPARING SUPERABSORBENT POLYMER AND SUPERABSORBENT POLYMER

CROSS REFERENCE TO RELATED APPLICATIONS

This application is a national phase entry under 35 U.S.C. § 371 of International Application No. PCT/KR2017/013612, filed Nov. 27, 2017, which claims priority to Korean Patent Application No. 10-2016-0177067, filed Dec. 22, 2016 and Korean Patent Application No. 10-2016-0177068, filed Dec. 22, 2016, the disclosures of which are incorporated herein by reference.

TECHNICAL FIELD

The present invention relates to a method for preparing superabsorbent polymer that exhibits excellent antibacterial activity, and simultaneously, can maintain or improve excellent absorption performance, and superabsorbent polymer obtained thereby.

BACKGROUND ART

Super absorbent polymer (SAP) is synthetic polymer material that has hydrophilic (COOH, COO$^-$Na$^+$) functional groups and can absorb moisture of 500 to 1000 times of self-weight, and is also named differently as super absorbency material (SAM), absorbent gel material (AGM), etc. according to developing companies. The superabsorbent polymer began to be commercialized as sanitary items, and currently, it is being widely used as hygienic goods such as a disposable diaper and so on, water-holding material for soil, water stop material for civil engineering and architecture, sheets for raising seedling, freshness preservatives in the field of food circulation, fomentation material, etc.

In most cases, such superabsorbent polymer is being widely used in the field of hygienic goods such as a diaper or sanitary pad, etc., and for such use, it is required to exhibit high absorption power to moisture, etc., and the absorbed moisture should not escape even under external pressure, and besides, it should properly maintain the shape even when it absorbs water and the volume is expanded (swollen), thus exhibiting excellent permeability.

In addition, odor as well as wearability after absorption is also an important problem in superabsorbent polymer for a diaper. Thus, in order to inhibit odor generated due to the materials produced by the metabolism of microorganisms existing in urine and feces, there is a need for the development of antibacterial superabsorbent polymer.

However, in the case of superabsorbent polymers developed so far, even if they exhibit antibacterial activities, there was a limit to the maintenance or improvement in both CRC, AUP excellently.

And, since ammonia produced by bacterial proliferation and urine and feces existing in hygienic materials after use may induce unpleasant feelings and skin rash to consumers, it is very important to introduce deodorant and antibacterial activities in superabsorbent polymer, and studies thereon are being actively progressed.

However, most of the studies introduce additives with excellent antibacterial properties in superabsorbent polymer to kill bacteria, and such superabsorbent polymer may be harmful to human bodies and environments. Thus, it is very important to develop superabsorbent polymer that inhibits only proliferation of bacteria instead of killing them, by selecting optimum antibacterial material and controlling the amount.

Therefore, there is a continuous demand for the development of technology for providing superabsorbent polymer that not only maintains basic absorption properties excellently, but also has antibacterial activity.

DISCLOSURE

Technical Problem

It is an object of the present invention to provide a method for preparing superabsorbent polymer that has excellent antibacterial activity, in which basic absorption properties required for superabsorbent polymer are maintained or improved, and superabsorbent polymer obtained thereby.

It is another object of the present invention to provide a method for preparing superabsorbent polymer in which basic absorption properties required for superabsorbent polymer are maintained or improved, and simultaneously, which inhibits bacterial proliferation rather than killing bacteria, thus exhibiting optimal deodorant and antibacterial activities, and is harmless to human body and environment.

Technical Solution

The present invention provides a method for preparing superabsorbent polymer comprising the steps of conducting crosslinking polymerization of water soluble ethylenically unsaturated monomers having acid groups of which at least a part are neutralized, in the presence of an internal crosslinking agent, to form hydrogel polymer;

drying, grinding and sieving the hydrogel polymer to form base polymer powder; and surface crosslinking the base polymer powder using a surface crosslinking solution comprising a surface crosslinking agent and cuprous oxide as an antibacterial agent, wherein the cuprous oxide is included in the content of 0.001 to 2.5 parts by weight, based on 100 parts by weight of the base polymer powder.

The present invention also provides superabsorbent polymer comprising base polymer powder comprising crosslinked polymer of water soluble ethylenically unsaturated monomers having acid groups of which at least a part are neutralized; and a surface crosslink layer that is formed on the base polymer powder, and comprises cuprous oxide through a surface crosslinking agent, wherein CRC is 39 to 50 g/g, and AUP is 16 to 23 g/g.

The present invention also provides superabsorbent polymer comprising base polymer powder comprising crosslinked polymer of water soluble ethylenically unsaturated monomers having acid groups of which at least a part are neutralized; and a surface crosslink layer that is formed on the base polymer powder, and comprises cuprous oxide through a surface crosslinking agent, wherein CRC is 30 to 50 g/g, and AUP is 16 to 25 g/g, and in an antibacterial activity test using artificial urine containing $10^4$ CFU/ml of bacteria and nutrients, compared to superabsorbent polymer without cuprous oxide, at least 99% inhibition of bacterial proliferation is exhibited.

Hereinafter, superabsorbent polymer and preparation method thereof according to specific embodiments of the invention will be explained in detail. However, they are presented only as the illustrations of the invention, the scope of the invention is not limited thereby, and it is obvious to one of ordinary knowledge in the art that various modifications can be made to the embodiments within the scope of right of the invention.

In addition, the term "comprise" or "include" used in the specification means to include a constructional element (or constructional component) without specific limitations, and it cannot be interpreted as excluding the addition of other constructional elements (or constructional components).

According to one embodiment of the invention, a method for preparing superabsorbent polymer comprising the steps of conducting crosslinking polymerization of water soluble ethylenically unsaturated monomers having acid groups of which at least a part are neutralized, in the presence of an internal crosslinking agent, to form hydrogel polymer;

drying, grinding and sieving the hydrogel polymer to form base polymer powder; and surface crosslinking the base polymer powder using a surface crosslinking solution comprising a surface crosslinking agent and cuprous oxide (cuprous oxide) as an antibacterial agent, wherein the cuprous oxide is included in the content of 0.001 to 2.5 parts by weight, based on 100 parts by weight of the base polymer powder, is provided.

More specifically, according to the first embodiment of the present invention, a method for preparing superabsorbent polymer comprising the steps of: conducting crosslinking polymerization of water soluble ethylenically unsaturated monomers having acid groups of which at least a part are neutralized, in the presence of an internal crosslinking agent, to form hydrogel polymer; drying, grinding and sieving the hydrogel polymer to form base polymer powder; and surface crosslinking the base polymer powder using a surface crosslinking solution comprising a surface crosslinking agent and cuprous oxide) as an antibacterial agent, wherein the cuprous oxide is included in the content of 0.1 to 2.5 parts by weight, based on 100 parts by weight of the base polymer powder, and the superabsorbent polymer has CRC of 39 to 50 g/g and AUP of 16 to 23 g/g, is provided.

And, according to the first embodiment of the present invention, a method for preparing superabsorbent polymer comprising the steps of: conducting crosslinking polymerization of water soluble ethylenically unsaturated monomers having acid groups of which at least a part are neutralized, in the presence of an internal crosslinking agent, to form hydrogel polymer; drying, grinding and sieving the hydrogel polymer to form base polymer powder; and surface crosslinking the base polymer powder using a surface crosslinking solution comprising a surface crosslinking agent and cuprous oxide) as an antibacterial agent, wherein the cuprous oxide is included in the content of 0.001 to 0.1 parts by weight, based on 100 parts by weight of the base polymer powder, and the superabsorbent polymer exhibits at least 99% inhibition of bacterial proliferation, compared to superabsorbent polymer without cuprous oxide, in an antibacterial activity test using artificial urine containing $10^4$ CFU/ml of bacteria and nutrients, is provided.

Thus, the superabsorbent polymer of one embodiment may not also exhibit antibacterial activity, but also exhibit bacterial proliferation inhibition effect, by controlling the content of cuprous oxide included in the surface crosslinking solution within the above range. And, the method of the present invention can maintain previously known basic absorption properties or exhibit further improved properties, and can be very preferably applied for various hygienic goods such as a diaper, etc., due to antibacterial activity.

Hereinafter, a method for preparing superabsorbent polymer of one embodiment will be explained in more detail.

Commonly, superabsorbent polymer can be prepared by polymerizing water soluble ethylenically unsaturated monomers having acid groups of which at least a part are neutralized, such as a mixture of acrylic acid in which at least a part of carboxylic acid is neutralized with sodium salt, etc., and sodium salt thereof, in the presence of an internal crosslinking agent, and then, drying, grinding and sieving, and surface crosslinking using a surface crosslinking solution comprising a specific antibacterial agent.

However, if pollutants such as urine and feces are absorbed in the superabsorbent polymer, odors are generated by the pollutants, and thus, inhibition of odor is required well as excellent absorption function and wearability.

And, if pollutants such as urine and feces are absorbed in the superabsorbent polymer, bacterial is proliferated, and thus, a method of inhibiting bacterial proliferation is required. Namely, since a technology of completely removing bacteria as explained above may be harmful to human bodies and environments, studies on the development of a method capable of inhibiting only bacterial proliferation without influencing human bodies and environments have been progressed.

Thus, the present invention is aimed to provide superabsorbent polymer that has antibacterial activity, and simultaneously, can inhibit bacterial proliferation, in which basic properties including centrifuge retention capacity (CRC) and absorbency under pressure (AUP) are maintained/improved.

The method of the present invention comprises the steps of preparing base powder polymer using hydrogel polymer, and then, crosslinking the surface of the base polymer powder using a surface crosslinking solution comprising a surface crosslinking agent and cuprous oxide.

Here, the cuprous oxide ($Cu_2O$) added to the surface crosslinking solution functions as an antibacterial agent, and it provides antibacterial activity to the surface crosslink layer of base polymer and can basically improve the properties of superabsorbent polymer.

In the preparation method of one embodiment, the superabsorbent polymer may be obtained by conducting crosslinking polymerization of monomers in the presence of an internal crosslinking agent to obtain base polymer powder, and then, surface crosslinking the base polymer powder in the presence of a predetermined surface crosslinking agent, and the above described antibacterial agent within a certain content range.

Particularly, in the present invention, cuprous oxide may be used in the content of 0.001 to 2.5 parts by weight, based on 100 parts by weight of the base polymer, and within this range, antibacterial activity and selective bacterial proliferation inhibition effect can be realized.

And, the superabsorbent polymer using a specific amount of cuprous oxide in the surface crosslinking process may have largely improved centrifuge retention capacity (CRC), while absorbency under pressure (AUP) is maintained equivalent to or more excellent than the existing superabsorbent polymer or slightly lowered. Specifically, in the method of the present invention, the content of cuprous oxide may be 0.001 to 2.5 parts by weight, based on 100 parts by weight of the base polymer powder. If the content of cuprous oxide is less than 0.001 parts by weight, it may be difficult to exhibit antibacterial activity due to too small amount, and if it is greater than 2.5 parts by weight, AUP and permeability may sharply decrease.

And, according to the present invention, the cuprous oxide may be used in the content greater than or smaller than 0.1 parts by weight within the above range.

Thus, as necessary, the cuprous oxide may be used in the content of 0.1 to 2.5 parts by weight, or 0.001 to 0.1 parts by weight, based on 100 parts by weight of the base polymer powder.

According to the first embodiment, in case the cuprous oxide is used in the content of 0.1 to 2.5 parts by weight, based on 100 parts by weight of the base polymer powder, the content may be 0.2 to 1.0 parts by weight, or 0.4 to 0.6 parts by weight. If the content of the cuprous oxide is less than 0.1 parts by weight, although antibacterial activity may be exhibited, rapid increase in CRC may not be confirmed, and if it is greater than 2.5 parts by weight, AUP and permeability may rapidly decrease. Here, in order to exhibit more excellent CRC and AUP, it is more preferable to comprise at least 0.233 wt % to 2.5 parts by weight in the total composition. However, even if the cuprous oxide is included in the content less than 0.1 parts by weight, bacterial proliferation inhibition effect may be exhibited as explained below.

Thus, according to the second embodiment, in case the content of cuprous oxide is 0.001 to 0.1 parts by weight, bacterial proliferation inhibition effect may be exhibited, and basic properties of superabsorbent polymer equivalent to or more excellent than the existing superabsorbent polymer may be exhibited. If the content of cuprous oxide is less than 0.001 parts by weight, it may be difficult to exhibit antibacterial activity due to too small amount, and if it is greater than 0.1 parts by weight, extract content may increase. However, even if the content of cuprous oxide is 0.1 parts by weight or more, as long as it is within the range according to the present invention, rapid increase in CRC may be confirmed and deterioration of properties such as AUP may be prevented.

Namely, when the cuprous oxide is used during the surface crosslinking process, excellent inhibition effect of bacterial proliferation may be exhibited even with a very small amount. Thereby, the present invention provides excellent deodorant effect by inhibiting the generation of ammonia due to pollutants such as feces and urine.

And, in the present invention, an antibacterial test was progressed at a low bacterial concentration of $10^4$ CFU/ml instead of a high concentration of $10^6$ CFU/ml, and during the process of diluting pollutants containing $10^4$ CFU/ml of bacteria, nutrients were added to realize bacterial proliferation. For example, the pollutant may be artificial urine containing $10^4$ CFU/ml of bacteria and nutrients, wherein the nutrients may include Beef Nutrient. Thereafter, the artificial urine is diluted to an optimum concentration and cultured, and the number of colonies was observed to measure the inhibition effect of bacterial proliferation. By such a method, the present invention developed antibacterial superabsorbent polymer that inhibits bacterial proliferation only.

Preferably, the superabsorbent polymer according to the present invention may exhibit at least 99%, or 99.9% or more, or 99.95 to 99.98% bacterial proliferation inhibition, compared to superabsorbent polymer without cuprous oxide, in an antibacterial test using artificial urine containing $10^4$ to $10^6$ CFU/ml of bacteria and nutrients.

In addition, the superabsorbent polymer of the present invention may exhibit absorption properties such as absorbency under pressure (AUP), centrifuge retention capacity (CRC), etc., equivalent to or more excellent than the existing superabsorbent polymer.

And, the crystallite size of the cuprous oxide measured by XRD may be 20 to 55 nm. And, the average particle diameter of the cuprous oxide may be 0.001 µm to 45 µm.

And, in the surface crosslinking solution comprising a surface crosslinking agent and cuprous oxide, as the surface crosslinking agent, all the materials well known in this field may be used. For example, as the surface crosslinking agent, one or more selected from the group consisting of C3-20 polyhydric alcohol compounds, epoxy compounds, polyamine compounds, halo epoxy compounds and condensation products thereof, oxazoline-based compounds, mono-, di0 and poly-oxazolidinone compounds, cyclic urea compounds, multivalent metal salts, and C2-5 alkylene carbonate compounds may be used. According to preferable embodiment, an epoxy compound may be used as the surface crosslinking agent, and an epoxy crosslinking agent such as EX-810 may be used.

And, in the surface crosslinking solution, the surface crosslinking agent may be used in the content of 0.01 to 5 parts by weight, or 0.5 to 1 part by weight, or 0.1 to 0.3 parts by weight, based on 100 parts by weight of the base polymer powder.

And, when using the cuprous oxide, base polymer powder and a surface crosslinking solution comprising a surface crosslinking agent and cuprous oxide as an antibacterial agent may be mixed and stirred for a certain time to progress the surface crosslinking of base polymer powder. The stirring may be progressed at about 100 to 500 rpm for 5 to 30 minutes.

Meanwhile, in the preparation method of superabsorbent polymer of one embodiment, the water-soluble ethylenically unsaturated monomers may include one or more selected from the group consisting of anionic monomers and salts thereof such as acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid or 2-(meth)acrylamide-2-methyl propane sulfonic acid; non-ionic hydrophilic group containing monomers such as (meth)acrylamide, N-substituted (meth)acrylate, 2-hydroxyethyl (meth)acrylate, 2-hydroxypropyl (meth)acrylate, methoxy polyethylene glycol (meth)acrylate, or polyethylene glycol (meth) acrylate; and amino group containing unsaturated monomers such as (N,N)-dimethylaminoethyl (meth)acrylate, (N,N)-dimethylaminopropyl (meth)acrylamide, and quarternarized products thereof. Among them, acrylic acid or salts thereof, for example, acrylic acid of which at least a part is neutralized and/or alkali metal salts such as a sodium salt thereof may be used, and by using such monomers, superabsorbent polymer having more excellent properties can be prepared. In case the acrylic acid or alkali metal salt thereof is used as monomers, the acrylic acid may be neutralized with a basic compound such as caustic soda (NaOH) before use.

And, as the internal crosslinking agent for crosslinking polymerization of the monomers, one or more selected from the group consisting of C8-12 bis(meth)acrylamide, poly (meth)acrylate of C2-10 polyol, and poly(meth)allylether of C2-10 polyol may be used. More specifically, as the internal crosslinking agent, one or more pol(meth)acrylate of polyol selected from the group consisting of polyethyleneglycol di(meth)acrylate, polypropyleneoxy di(meth)acrylate, glycerin diacrylate, glycerin triacrylate and trimethylol triacrylate may be appropriately used. Among them, by using polyethyleneglycol di(meth)acrylate, etc. as the internal crosslinking agent, base polymer powder with an optimized internal crosslink structure and high gel strength may be obtained, and thereby, superabsorbent polymer fulfilling the properties of one embodiment may be more properly obtained.

And, the internal crosslinking agent may be used at a ratio of 0.005 moles or more, or 0.005 to 0.1 moles, or 0.005 to 0.05 moles, based on 1 mole of non-neutralized acrylic acid included in the monomers (or 0.3 parts by weight or more, or 0.3 to 0.6 parts by weight, based on 100 parts by weight of acrylic acid). Within such content ranges of the internal crosslinking agent, base polymer powder with high gel strength before surface crosslinking may be appropriately obtained, and superabsorbent polymer with excellent properties may be obtained through the method of one embodiment, And, after crosslinking polymerization of the monomers using the internal crosslinking agent, base polymer powder may be obtained through the processes of drying, grinding and sieving, etc., and it is appropriate that the base polymer powder and superabsorbent polymer obtained therefrom are prepared and provided so as to have a particle diameter of 150 to 850 μm through the processes of grinding and sieving, etc. More specifically, at least 95 wt % of the base polymer powder and superabsorbent polymer obtained therefrom may have a particle diameter of 150 to 850 μm, and less than 3 wt % may be fine powder having a particle diameter less than 150 μm.

Since the particle diameter distributions of the base polymer powder and superabsorbent polymer are controlled within preferable ranges, the superabsorbent polymer may exhibit the above explained excellent properties.

Meanwhile, the method of the above explained embodiment will be explained according to each step in more detail. However, since the monomers, internal crosslinking agent, antibacterial agent and particle diameter distribution, etc. have been already explained, the explanations thereof are omitted, and the remaining process constructions and conditions will be explained according to steps.

The preparation method superabsorbent polymer may comprise the steps of: progressing thermal polymerization or photopolymerization of a monomer composition comprising water soluble ethylenically unsaturated monomers, an internal crosslinking agent and a polymerization initiator to form hydrogel polymer comprising crosslinked polymer; drying the hydrogel polymer; grinding and sieving the dried polymer to form base polymer powder; and surface crosslinking the base polymer powder using an antibacterial surface crosslinking solution comprising a surface crosslinking agent, in the presence of cuprous oxide.

In the preparation method, the monomer composition comprises water soluble ethylenically unsaturated monomers, an internal crosslinking agent and a polymerization initiator, wherein the kind of monomers has been already explained above.

And, in the composition, the concentration of the water-soluble ethylenically unsaturated monomers may be controlled to about 20 to about 60 wt %, or about 40 to about 50 wt %, based on the monomer composition comprising the above explained raw materials and a solvent, and may be appropriately controlled considering polymerization time and reaction conditions, etc. However, if the concentration of the monomers becomes too low, yield of superabsorbent polymer may decrease, thus causing economical problems, and if the concentration becomes too high, process problems may be generated such as precipitation of a part of the monomers or low grinding efficiency of polymerized hydrogel polymer, etc., and the properties of superabsorbent polymer may be deteriorated.

And, the polymerization initiator is not specifically limited as long as it is commonly used for the preparation of superabsorbent polymer.

Specifically, as the polymerization initiators, a thermal polymerization initiator or a photopolymerization initiator according to UV irradiation may be used according to polymerization methods. However, even in the case of photopolymerization, since a certain amount of heat is generated by UV irradiation, etc., and heat is generated to some degree according to the progression of an exothermic polymerization reaction, a thermal polymerization initiator may be additionally included.

The photopolymerization initiator is not limited in terms of its construction, as long as it is a compound capable of forming a radical by light such as UV.

As the photopolymerization initiator, one or more selected from the group consisting of benzoin ether, dialkyl acetophenone, hydroxyl alkylketone, phenyl glyoxylate, benzyl dimethyl Ketal, acyl phosphine, and α-aminoketone may be used. As the specific example of the acyl phosphine, commercially used lucirin TPO, namely, 2,4,6-trimethyl-benzoyl-trimethyl phosphine oxide may be used. More various photopolymerization initiators are described in Reinhold Schwalm, "UV Coatings: Basics, Recent Developments and New Application (Elsevier 2007)", page 115, and are not limited to the above described examples.

The photopolymerization initiator may be added in the concentration of about 0.01 to about 1.0 wt %, based on the monomer composition. If the concentration of the photopolymerization initiator is too low, polymerization speed may become slow, and if the concentration of the polymerization initiator is too high, the molecular weight of the superabsorbent polymer may become small and the properties may become nonuniform.

And, as the thermal polymerization initiator, at least one selected from the group consisting of a persulfate initiator, an azo initiator, hydrogen peroxide, and ascorbic acid may be used. Specific examples of the persulfate initiator may include sodium persulfate ($Na_2S_2O_8$), potassium persulfate ($K_2S_2O_8$), ammonium persulfate (($NH_4)_2S_2O_8$), etc., and, specific examples of the azo initiator may include 2,2-azobis (2-amidinopropane)dihydrochloride, 2,2-azobis-(N,N-dimethylene)isobutyramidinedihydrochloride, 2-(carbamoylazo)isobutyronitril, 2,2-azobis[2-(2-imidazolin-2-yl) propane]dihydrochloride, 4,4-azobis-(4-cyanovalericacid), etc. More various thermal initiators are described in "Principle of Polymerization (Wiley, 1981)", Odian, page 203, and are not limited to the above described examples.

The thermal polymerization initiator may be included in the concentration of about 0.001 to about 0.5 wt %, based on the monomer composition. If the concentration of the thermal polymerization initiator is too low, additional thermal polymerization may hardly occur, and thus, the effect obtained by the addition of the thermal polymerization initiator may be insignificant, and if the concentration of the thermal polymerization initiator is too high, the molecular weight of the superabsorbent polymer may become small, and the properties may become non-uniform.

And, the kind of the internal crosslinking agent included in the monomer composition have been already explained above, and such an internal crosslinking agent may be included at the concentration of 0.01 to 0.5 wt %, based on the monomer composition, thus crosslinking the polymerized polymer. And, as explained above, the internal crosslinking agent may be used at a ratio of 0.005 moles or more, or 0.005 to 0.1 moles, or 0.005 to 0.05 moles, based on 1 mole of non-neutralized acrylic acid included in the monomers (or 0.3 parts by weight or more, or 0.3 to 0.6 parts by weight, based on 100 parts by weight of acrylic acid). Within such content ranges of the internal crosslinking agent, high gel strength of base polymer powder may be properly achieved, and superabsorbent polymer fulfilling the properties of the above explained embodiment may be prepared using the same.

The monomer composition may further comprise additives such as a thickener, a plasticizer, a preservation stabilizer, an antioxidant, etc., as necessary.

The above explained raw materials such as water soluble ethylenically unsaturated monomers, photopolymerization initiator, thermal polymerization initiator, internal crosslinking agent and additives may be prepared in the form of a monomer composition solution dissolved in a solvent.

Here, the solvent that can be used is not limited in terms of its construction as long as it can dissolve or disperse the above explained components, and for example, one or more selected from water, ethanol, ethyleneglycol, diethyleneglycol, triethyleneglycol, 1,4-butanediol, propyleneglycol, ethyleneglycol monobutyl ether, propyleneglycol monomethyl ether, propyleneglycol monomethyl ether acetate, methylethylketone, acetone, methylamylketone, cyclohexanone, cyclopentanone, diethyleneglycol monomethyl ether, diethyleneglycol ethyl ether, toluene, xylene, butyrolactone, carbitol, methylcellosolve acetate and N,N-dimethylacetamide, etc. may be used alone or in combination.

The solvent may be included in the remaining amount excluding the above-explained components, based on the total amount of the monomer composition.

Meanwhile, a method of forming hydrogel polymer by the thermal polymerization or photopolymerization of the monomer composition is not specifically limited in terms of its construction, as long as it is a commonly used polymerization method.

Specifically, the polymerization method is largely classified into thermal polymerization and photopolymerization according to energy source, and commonly, thermal polymerization may be progressed in a reactor equipped with a stirring axis such as a kneader, and photopolymerization may be progressed in a reactor equipped with a movable conveyer belt, but the above explained polymerization methods are no more than examples, and the present invention is not limited thereto.

For example, hydrogel polymer may be obtained by supplying hot air into a reactor equipped with a stirring axis such as a kneader or heating the reactor, thus progressing thermal polymerization, and the hydrogel polymer discharged to the outlet of the reactor may be in the form of a few centimeters to a few millimeters according to the shape of the stirring axis equipped in the reactor. Specifically, the size of obtained hydrogel polymer may vary according to the concentration of the introduced monomer composition and the introduction speed, etc., and commonly, hydrogel polymer having a particle size of 2 to 50 mm may be obtained.

And, in case photopolymerization is progressed in a reactor equipped with a movable conveyer belt as explained above, the obtained hydrogel polymer may be in the form of a sheet having the width of the belt. Here, the thickness of the polymer sheet may vary according to the concentration of the introduced monomer composition and the introduction speed, but, commonly, a monomer composition is preferably fed such that polymer in the form of a sheet having a thickness of about 0.5 cm to about 5 cm may be obtained. In case a monomer composition is fed such that the thickness of sheet-shaped polymer may be too thin, production efficiency may be low, and if the thickness of the sheet-shaped polymer is greater than 5 cm, due to the too thick thickness, a polymerization reaction may not uniformly occur throughout the whole thickness.

Here, the moisture content of hydrogel polymer obtained by such a method may be 40 to 80 wt %. Throughout the specification, the "moisture content" is the content of moisture occupied based on the total weight of hydrogel polymer, and it means a value obtained by subtracting the weight of polymer of a dry state from the weight of hydrogel polymer. Specifically, it is defined as a value calculated by measuring the weight loss according to moisture evaporation in the polymer while raising the temperature of polymer through infrared heating to dry. At this time, the drying condition is established such that the temperature is raised from room temperature to about 180° C. and then maintained at 180° C., and the total drying time is 20 minutes including a temperature raising step of 5 minutes.

Next, the obtained hydrogel polymer is dried.

At this time, if necessary, in order to increase the efficiency of the drying step, a step of coarse grinding may be conducted before drying.

Here, grinders that can be used in the coarse grinding is not limited in terms of the constructions, but specifically, one selected from the group consisting of a vertical pulverizer, a turbo cutter, a turbo grinder, a rotary cutter mill, a cutter mill, a disc mill, a shred crusher, a crusher, a chopper, a disc cutter may be used, but is not limited thereto.

The coarse grinding step may be progressed such that the particle diameter of hydrogel polymer may become 2 to 15 mm.

Grinding to a particle diameter of less than 2 mm would not be technically easy due to the high moisture content of the hydrogel polymer, and may generate agglomeration between the ground particles. Meanwhile, if grinding to a particle diameter greater than 15 mm, the effect of increasing the efficiency of the subsequent drying step may be insignificant.

The hydrogel polymer coarsely ground as explained above, or hydrogel polymer immediately after polymerization that does not pass through the coarse grinding step is dried, and the drying temperature may be about 150° C. to about 250° C. If the drying temperature is less than about 150° C., a drying time may too lengthen, and the properties of the finally prepared superabsorbent polymer may be deteriorated, and if the drying temperature is greater than about 250° C., only the surface of hydrogel polymer may be dried, thus generating fine powder in the subsequent grinding process, and the properties of the finally prepared superabsorbent polymer may be deteriorated. Preferably, the drying may be progressed at a temperature of about 150 to 200° C., more preferably at 160 to 180° C.

Meanwhile, the drying may be progressed for 20 minutes to 90 minutes considering the process efficiency, etc., but the drying time is not limited thereto.

And, the drying method is not limited in terms of the construction as long as it can be commonly used as a drying process of hydrogel polymer. Specifically, the drying step may be progressed by hot wind supply, infrared ray irradiation, ultrahigh frequency wave irradiation, or UV irradiation, etc. The polymer dried by such a method may exhibit a moisture content of about 0.1 to about 10 wt %.

Next, a step of grinding the dried polymer obtained through the drying step is conducted.

The particle diameter of the polymer powder obtained after the grinding step may be 150 μm to 850 μm. As a grinder for grinding to such a particle diameter, specifically, a pin mill, a hammer mill, a screw mill, a roll mill, a disc mill, or a jog mill, etc. may be used, but the grinder is not limited thereto.

And, in order to manage the properties of the finally productized superabsorbent polymer after the grinding step, a step of sieving the polymer powder obtained after grinding according to the particle diameter may be conducted. Preferably, polymer with a particle diameter of 150 μm to 850 μm may be sieved, and only the polymer powder having such particle diameters may be additionally passed through a step of surface cross linking reaction and productized. The particle diameter distribution of the base polymer powder obtained through the process has been already explained above, and the detailed explanation thereof is omitted.

Meanwhile, after obtaining base polymer powder through the above explained grinding and/or sieving processes, superabsorbent polymer of one embodiment may be prepared through a surface crosslinking process. The cuprous oxide, which is an antibacterial agent usable in the surface crosslinking process, has been already explained above, and the explanation thereof is omitted.

In the surface crosslinking process, for example, in the presence of an antibacterial surface crosslinking solution comprising the cuprous oxide and the surface crosslinking agent, the base polymer powder may be heat treated to surface crosslink.

And, in the surface crosslinking step, examples of the materials that can be used as a surface crosslinking agent are as explained above.

In addition, the surface crosslinking solution may further comprise water and/or methanol. Thereby, the surface crosslinking agent and antibacterial particles may be uniformly dispersed in the base polymer powder. Here, the ratio of water and methanol based on 100 parts by weight of the base polymer powder may be controlled so as to uniformly disperse the surface crosslinking agent and the cuprous oxide providing antibacterial activity, prevent agglomeration of base polymer powder, and optimizer the surface penetration depth of the surface crosslinking agent.

Meanwhile, the surface crosslinking step may be conducted by a heating reaction at a temperature of 140 to 200° C. for 5 to 80 minutes. Preferably, the surface crosslinking reaction may be progressed by heat treating base polymer powder to which the surface crosslinking solution is added at a maximum reaction temperature of 140° C. to 200° C., or 150° C. to 190° C. for 5 to 80 minutes, or 10 to 70 minutes, or 20 to 60 minutes. More specifically, the surface crosslinking step may be progressed by raising the temperature from the initial temperature of 20° C. to 130° C., or 40° C. to 120° C. to the above maximum reaction temperature over 10 to 40 minutes, and maintaining the maximum temperature for 5 to 80 minutes and heat treating.

By such surface crosslinking process conditions, superabsorbent polymer properly fulfilling excellent antibacterial activity and absorption properties of CRC, AUP, etc. may be prepared.

A means to increase temperature for surface crosslinking is not specifically limited. A heating medium may be supplied, or a heat source may be directly supplied to heat. Here, the kind of heating medium that can be used may include steam, hot air, temperature-risen fluid such as hot oil, etc., but the present invention is not limited thereto, and the temperature of supplied heating medium may be appropriately selected considering the means of heating medium, temperature rise speed and target temperature to be raised. Meanwhile, as the directly supplied heat source, electric heating, gas heating, etc. may be mentioned, but the present invention is not limited thereto.

Meanwhile, according to the above explained method, superabsorbent polymer having excellent antibacterial activity and exhibiting bacterial proliferation inhibition effect may be provided.

According to one embodiment of the invention, if the antibacterial agent is used in the content of 0.1 parts by weight or more and less than 2.5 parts by weight, based on 100 parts by weight of base polymer, superabsorbent polymer with excellent antibacterial activity and excellent basic properties may be provided.

Thus, superabsorbent polymer comprising base polymer powder comprising crosslinked polymer of water soluble ethylenically unsaturated monomers having acid groups of which at least a part are neutralized; and a surface crosslinking layer that is formed on the base polymer powder, and comprises cuprous oxide through a surface crosslinking agent, wherein CRC is 39 to 50 g/g, and AUP is 16 to 23 g/g, is provided.

And, according to another embodiment of the invention, if the antibacterial agent is used in the content of 0.001 parts by weight or more and less than 0.1 parts by weight, based on 100 parts by weight of base polymer, bacterial proliferation inhibition effect may be exhibited as well as antibacterial activity.

Thus, the present invention provides superabsorbent polymer comprising base polymer powder comprising crosslinked polymer of water soluble ethylenically unsaturated monomers having acid groups of which at least a part are neutralized; and a surface crosslinking layer that is formed on the base polymer powder, and comprises cuprous oxide through a surface crosslinking agent, wherein CRC is 30 to 50 g/g, and AUP is 16 to 25 g/g.

And, as explained above, the cuprous oxide, which is an antibacterial material, may be included and dispersed in the crosslink structure of the surface crosslink layer, or may exist while being embedded in the surface crosslink layer.

Such superabsorbent polymer may have antibacterial activity, and simultaneously, the properties such as CRC, AUP, etc. may be maintained or improved. The properties of the supersabsorbent polymer may be defined by each property value explained below.

First, the centrifuge retention capacity (CRC) of the superabsorbent polymer may be 30 to 50 g/g or 39 to 50 g/g, or 42 to 45 g/g.

As such, the superabsorbent polymer prepared by one embodiment may exhibit excellent absorption property under no load.

The centrifuge retention capacity (CRC) to a saline solution may be calculated by the following Formula 1, after absorbing a saline solution in superabsorbent polymer for 30 minutes.

$$CRC(g/g)=\{[W_2(g)-W_1(g)-W_0(g)]/W_0(g)\} \quad \text{[Formula 1]}$$

In the Formula 1, $W_0(g)$ is the initial weight(g) of superabsorbent polymer, $W_1(g)$ is the weight of an apparatus, measured after soaked in a saline solution for 30 minutes to absorb, and then, drained at 250 G for 3 minutes using a centrifuge, without superabsorbent polymer, and $W_2(g)$ is the weight of an apparatus including superabsorbent polymer, measured after soaking superabsorbent polymer in a saline solution to absorb for 30 minutes at room temperature, and then, draining at 250 G for 3 minutes using a centrifuge.

And, in case the amount of the antibacterial agent used is 0.1 to 2.5 parts by weight, the absorbency under pressure (AUP) of the superabsorbent polymer may be 16 to 23 g/g, or 16 to 21 g/g. And, if the amount of the antibacterial agent used is 0.001 to 0.1 parts by weight, the absorbency under pressure (AUP) of the superabsorbent polymer may be 16 to 25 g/g.

As such, the superabsorbent polymer may exhibit excellent absorption property even under load.

The absorbency under pressure (AUP) may be calculated according to the following Formula 2, after absorbing a saline solution in superabsorbent polymer under load of 0.7 psi for 1 hour:

$$AUP(g/g)=[W_4(g)-W_3(g)]/W_0(g) \quad \text{[Formula 2]}$$

In the Formula 2, $W_0(g)$ is the initial weight (g) of superabsorbent polymer, $W_3(g)$ is the sum of the weight of superabsorbent polymer and the weight of the apparatus capable of giving load to the superabsorbent polymer, and $W_4(g)$ is the sum of the weight of superabsorbent polymer and the weight of the apparatus capable of giving load to the superabsorbent polymer, after absorbing a saline solution in the superabsorbent polymer under load (0.7 psi) for 1 hour.

Preferably, in the step of surface crosslinking, when the cuprous oxide is included in the content of 0.5 parts by weight, based on 100 parts by weight of the base polymer powder, CRC may become 44.7 g/g, and AUP may become 20.4 g/g. In this case, all the absorption properties may be improved, and excellent antibacterial activity may also be provided.

As such, the superabsorbent polymer may exhibit excellent basic absorption property and absorption performances such as absorbency under load, etc.

And, if the amount of the antibacterial agent used is 0.001 to 0.1 parts by weight, the superabsorbent polymer may exhibit excellent bacterial proliferation inhibition effect, in an antibacterial test using artificial urine containing $10^4$ CFU/ml of bacteria and nutrients, as explained above.

As explained above, the superabsorbent polymer obtained according to one embodiment may have excellent antibacterial activity, and simultaneously, the basic properties such as centrifuge retention capacity and absorbency under pressure, etc. required in superabsorbent polymer may be maintained or improved. And, the superabsorbent polymer of the present invention may also exhibit bacterial proliferation inhibition, thus improving deodorant activity. Thus, it may be appropriately used for hygienic goods such as a diaper, a sanitary pad, etc.

Advantageous Effects

According to the present invention, a method for preparing superabsorbent polymer having antibacterial activity, in which properties such as centrifuge retention capacity, absorbency under pressure are maintained excellent or improved, and superabsorbent polymer prepared thereby are provided.

And, the present invention provides a method for preparing superabsorbent polymer that exhibits properties such as centrifuge retention capacity, absorbency under load, etc. equivalent to or more excellent than the existing superabsorbent polymer, and simultaneously, can exhibit bacterial proliferation and has excellent antibacterial activity, and superabsorbent polymer prepared thereby.

Particularly, since such superabsorbent polymer inhibits ammonia generation due to feces and urine and bacterial proliferation, thus exhibiting excellent deodorant and antibacterial activities, it can increase wearability of consumers and inhibit skin rashes.

Thus, the superabsorbent polymer may be appropriately used for hygienic goods such as a diaper, etc.

BRIEF DESCRIPTION OF THE DRAWINGS

FIG. 1 compares and shows CRC and AUP absorption properties according to the contents of cuprous oxide of Comparative Example 1 and Examples 1 to 7 according to one embodiment of the present invention.

FIG. 2 compares and shows the antibacterial test result photographs of the superabsorbent polymers of Comparative Example 5 and Examples 8 to 9 according to one embodiment of the present invention.

DETAILED DESCRIPTION OF THE EMBODIMENTS

Hereinafter, the actions and effects of the invention will be explained in more detail through specific examples. However, these examples are presented only as the illustrations of the invention, and the scope of the invention is not determined thereby.

And, in the Examples and Comparative Examples below, each property of superabsorbent polymer was measured and evaluated by the following method.

(1) Evaluation of Particle Diameter

The particle diameters of base polymer powder and superabsorbent polymer used in Examples and Comparative Examples were measured according to the method of EDANA WSP 220.3 of EDANA (European Disposables and Nonwovens Association) Standard.

(2) Centrifuge Retention Capacity (CRC)

For the superabsorbent polymers of Examples and Comparative Examples, centrifuge retention capacity (CRC) by the absorption scale under no load was measured according to EDANA WSP 241.3 of EDANA (European Disposables and Nonwovens Association) standard.

Specifically, W (g, about 0.2 g) of the polymers of Examples and Comparative Examples were uniformly put in an envelope made of non-woven fabric and sealed, and then, soaked in a saline solution consisting of 0.9 wt % sodium chloride aqueous solution at room temperature. After 30 minutes, the envelope was drained at 250 G for 3 minutes using a centrifuge, and then, the mass W2(g) of the envelope was measured. And, after the same operation without using polymer, the mass W1(g) at that time was measured.

Using the obtained masses, CRC (g/g) was calculated according to the following Formula 1.

$$CRC(g/g)=\{[W_2(g)-W_1(g)-W_0(g)]/W_0(g)\} \quad \text{[Formula 1]}$$

In the Formula,

W(g) is the initial weight of superabsorbent polymer (g),

W1(g) the weight of the apparatus without superabsorbent polymer, measured after soaked in a saline solution for 30 minutes, and then, drained using a centrifuge at 250 G for 3 minutes, and W2(g) is the weight of the apparatus including superabsorbent polymer, measured after the superabsorbent polymer is soaked in a saline solution at room temperature for 30 minutes, and then, drained using a centrifuge at 250 G for 3 minutes.

(3) Absorbing Under Pressure (AUP)

For the superabsorbent polymers of Examples and Comparative Examples, absorbency under load was measured according to EDANA WSP 242.3 of EDANA (European Disposables and Nonwovens Association) standard.

First, 400 mesh wire netting made of stainless was installed on the bottom of a plastic cylinder with an inner diameter of 60 mm. Under the conditions of temperature of 23±2° C. and relative humidity of 45%, $W_0$(g, 0.90 g) of the polymers obtained in Examples 1~6 and Comparative Examples 1~3 were uniformly scattered on the wire netting, and a piston that can uniformly give a load of 4.83 kPa (0.7 psi) and has an outer diameter slightly smaller than 60 mm was installed thereon without a gap with the inner wall of the cylinder such that the movement upward and downward was not hindered. At this time, the weight $W_3$(g) of the apparatus was measured.

On the inner side of a petri dish with a diameter of 150 mm, a glass filter with a diameter of 125 mm and a thickness of 5 mm was positioned, and a saline solution consisting of 0.90 wt % sodium chloride was put to the same level as the top of the glass filter. One filter paper with a diameter of 120 mm was put thereon. On the filter paper, the above measuring apparatus was mounted, and liquid was absorbed under load for 1 hour. After 1 hour, the measuring apparatus was raised, and the weight $W_4$(g) was measured.

Using the obtained masses, AUP (g/g) was calculated according to the Formula 2, thus confirming absorbency under pressure.

$$AUP(g/g)=[W_4(g)-W_3(g)]/W_0(g) \quad \text{[Formula 2]}$$

In the Formula 2, $W_0$(g) is the initial weight (g) of superabsorbent polymer, $W_3$(g) is the sum of the weight of superabsorbent polymer and the weight of the apparatus capable of giving load to the superabsorbent polymer, and $W_4$(g) is the sum of the weight of superabsorbent polymer and the weight of the apparatus capable of giving load to the superabsorbent polymer, after absorbing a saline solution in the superabsorbent polymer under load (0.7 psi) for 1 hour.

(4) Permeability

While a piston is put in a chromatography column (Φ20 mm), lines were marked at the fluid surfaces of fluid volumes 20 ml, 40 ml. About 10 ml of a saline solution was filled, 0.2 g of superabsorbent polymer (30#~50#) was put, and then, a saline solution was added to the total volume of 50 ml. It was allowed to stand for 30 minutes such that superabsorbent polymer may be sufficiently swollen. In the chromatography column, a piston with a weight (0.3 psi) was put, and allowed to stand for 1 minute. After opening the stopper at the bottom of the column, a time taken until the fluid surface was at the marked line of 20 ml from 40 ml (T1:sec) was reported.

After repeating 4.2~4.5 with a blank without superabsorbent polymer, a time taken (B1) was reported.

$$\text{Permeability(sec.)}=T1-B1 \quad \text{[Formula 3]}$$

(5) Vortex Test 50.0±1.0 mL of a 0.9% NaCl solution was added to a 100 mL beaker. A cylindrical stirring bar (30×6 mm) was put, and the solution was stirred at 600 rpm on a stirring plate. 2.000±0.010 g of moisture absorbing polymer particles were added to the beaker at a time as soon as possible, and when the addition began, a stop watch was started. The stop watch was stopped when the surface of the mixture becomes a still state, wherein the state means that the surface does not have a turbulent flow, and at this time, although the mixture still rotates, the whole surface of the particles may rotate as one unit. A time marked by the stop watch was reported as a vortex time.

(6) 16 h EC (Extractable Content)

Using 3 kinds of buffer solutions, pH electrode calibration was conducted. Using a cylinder, 200 mL of a saline solution was put into a 250 mL beaker or conical flask. On a balance, a dried weighing vessel was put, and a 0 point was adjusted. Thereafter, 0.95~1.05 g of superabsorbent polymer was put on the weighing vessel, and a 0 point was adjusted again. Into the flask containing 200 mL of a saline solution, the superabsorbent polymer was uniformly introduced. And then, the weighing vessel was put on the balance again. The negative weight marked in the balance is the weight of the sample practically introduced. After sealing the (m) flask, the solution was stirred at 250±50 rpm for 16 hours. As a blank, 200 mL of a saline solution was prepared in the same container. After the stirring was finished, it was allowed to stand for about 10 minutes such that gel was completely settled on the container. After filtering the gel using 10 filter papers, 100 mL of supernatant in a solution state was obtained.

For the measurement of the result, 50 mL of the sample solution was taken, and 50 mL of the aliquoted blank filtered solution was taken. The amount (Vab) of 50 mL of the aliquoted blank filtered solution, of which pH reached 10.0 with a standard NaOH solution, was measured, and then, the titration amount (Vbb) of the titrated solution, of which pH reached 2.7 with a standard HCl solution, was measured. The amount (Va) of 50 mL of the aliquoted sample filtered solution, of which pH reached 10.0 with a standard NaOH solution, was measured, and then, the titration amount (Vb) of the titrated solution, of which pH reached 2.7 with a standard HCl solution, was measured.

The amount of carboxylic acid (Na) was calculated as follows.

$$Na(\text{Moles})=[(Va-Vab)\times Ca]/1000 \quad \text{[Formula 4]}$$

(in the Formula, Va and Vab are as explained above, and Ca is the molarity of base (0.1 mol/l NaOH))

The total amount of carboxylate (N1) was calculated as follows.

$$N1(\text{Moles})=[(Vb-Vbb)\times Cb]/1000 \quad \text{[Formula 5]}$$

(in the Formula, Vb and Vbb are as explained above, and Cb is the molarity of acid (0.1 mol/l HCl))

The amount of neutralized carboxylate (Nb) was calculated as follows.

$$Nb(\text{Moles})=N1-Na \quad \text{[Formula 6]}$$

(in the Formula, N1 is the total amount of carboxylate measured by the Formula 4, and Na is the amount of carboxylic acid measured by the Formula 3)

The amount of carboxylic acid (Wa) and the amount of sodium carboxylate (Wb) were calculated as follows.

$$Wa(g)=Na\times Ma\times D$$

$$Wb(g)=Nb\times Mb\times D \quad \text{[Formula 7]}$$

(in the Formula, Na and Nb are as explained above, Ma is the molecular weight of acrylic acid (72 g/mol), Mb is the molecular weight of acrylate (94 g/mol), and D a dilution coefficient (200/50=4))

The water soluble content (W) of superabsorbent polymer was calculated as follows.

$$W(\%)=[(Wa+Wb)\times 100]/m \quad \text{[Formula 8]}$$

(in the Formula, Wa and Wb are as explained above, and m is the amount of a sample (g))

From the obtained results, average water soluble content of the sample was calculated.

(7) 1 h EC

Using 3 kinds of buffer solutions, pH electrode calibration was conducted. Using a cylinder, 200 mL of a saline solution was put into a 250 mL beaker or conical flask. On a balance, a dried weighing vessel was put, and a 0 point was adjusted. Thereafter, 0.95~1.05 g of superabsorbent polymer was put on the weighing vessel, and a 0 point was adjusted again. Into the flask containing 200 mL of a saline solution, the superabsorbent polymer was uniformly introduced. And then, the weighing vessel was put on the balance again. The negative weight marked by the balance is the weight of the sample practically introduced. After sealing the (m) flask, the solution was stirred at 250±50 rpm for 1 hour. As a blank, 200 mL of a saline solution was prepared in the same container. After the stirring was finished, it was allowed to stand for about 10 minutes such that gel was completely settled on the container. After filtering the gel using 10 filter papers, 100 mL of supernatant in a solution state was obtained.

For the measurement of the result, 50 mL of the sample solution was taken, and 50 mL of the aliquoted blank filtered solution was taken. The amount (Vab) of 50 mL of the aliquoted blank filtered solution, of which pH reached 10.0 with a standard NaOH solution, was measured, and then, the titration amount (Vbb) of the titrated solution, of which pH reached 2.7 with a standard HCl solution, was measured. The amount (Va) of 50 mL of the aliquoted sample filtered solution, of which pH reached 10.0 with a standard NaOH solution, was measured, and then, the titration amount (Vb) of the titrated solution, of which pH reached 2.7 with a standard HCl solution, was measured.

The amount of carboxylic acid (Na) was calculated as follows.

$$Na(\text{Moles}) = [(Va - Vab) \times Ca]/1000 \quad \text{[Formula 9]}$$

(in the Formula, Va and Vab are as explained above, and Ca is the molarity of base (0.1 mol/l NaOH))

The total amount of carboxylate (N1) was calculated as follows.

$$N1(\text{Moles}) = [(Vb - Vbb) \times Cb]/1000 \quad \text{[Formula 10]}$$

(in the Formula, Vb and Vbb are as explained above, and Cb is the molarity of acid (0.1 mol/l HCl))

The amount of neutralized carboxylate (Nb) was calculated as follows.

$$Nb(\text{Moles}) = N1 - Na \quad \text{[Formula 11]}$$

(in the Formula, N1 is the total amount of carboxylate measured by the Formula 4, and Na is the amount of carboxylic acid measured by the Formula 3)

The amount of carboxylic acid (Wa) and the amount of sodium carboxylate (Wb) were calculated as follows.

$$Wa(g) = Na \times Ma \times D$$

$$Wb(g) = Nb \times Mb \times D \quad \text{[Formula 12]}$$

(in the Formula, Na and Nb are as explained above, Ma is the molecular weight of acrylic acid (72 g/mol), Mb is the molecular weight of acrylate (94 g/mol), and D a dilution coefficient (200/50=4))

The water soluble content (W) of superabsorbent polymer was calculated as follows.

$$W(\%) = [(Wa + Wb) \times 100]/m \quad \text{[Formula 13]}$$

(in the Formula, Wa and Wb are as explained above, and m is the amount of a sample (g))

From the obtained results, average water soluble content of the sample was calculated.

(8) N.D.

N.D. means the amount of carboxylic acid neutralized in the test (7).

(9) Residual Monomers (RM)

1.0 g (±0.005 g) of SAP was put into a 250 mL flask beaker containing 200 g of 0.9% saline solution. Using a magnetic bar, the solution was stirred at 500 rpm for 60 minutes. After stirring, it was allowed to stand for 5 minutes, and the liquid in the upper layer was filtered with a 0.45 μm filter. Thereafter, a calibration curve was set with acrylic acid, and then, the concentration of RM was measured with HPLC (Ref. measuring method: WSP210.2(ERT410.2-02), ISO 17190-2:2001).

(11) CFU Analysis (Antibacterial Test)

2 mL of artificial urine containing $10^4$ CFU/ml of bacterial and nutrients was mixed with 0.1 g of superabsorbent polymer to prepare gel. Thereafter, it was stirred at 25° C. at 110 rpm with a stirrer, while putting a weight to apply a pressure of 0.7 psi. The stirring time was limited to maximum 12 hours. After stirring, it was washed with 18 mL of a 0.9% saline solution, and then, diluted to an optimum concentration. Thereafter, it was applied on agar medium previously prepared, and cultured for 18 hours, and then, the number of colonies was reported and the concentration was calculated.

Examples 1 to 7

For the case wherein a surface crosslinking solution comprises cuprous oxide in the content of 0.1 parts by weight or more to 2.5 parts by weight, based on 100 parts by weight of base polymer powder, experiments were progressed.

Specifically, in a reactor, 100 g of acrylic acid, 36.2 g of sodium hydroxide, 0.21 g of polyethyleneglycol diacrylate (Mw=598) as a crosslinking agent, 0.008 g of diphenyl(2,4,6-trimethylbenzoyl)-phosphine oxide as UV initiator, 0.03 g of modified clay additive (0.03 parts by weight), and 121.5 g of water were mixed to prepare a water-soluble unsaturated monomer composition with an acrylic acid monomer concentration of 36.7 wt %.

Here, as the modified clay additive, garamite 2578, which is a mixed product with plate and rod structures, was used. The garamite 2578 is a commercial product of platelet and rod-shaped clay that is modified by an amine-based organic compound of quaternary alkylammonium ion type and has an amine group introduced on the surface, wherein based on 100 parts by weight of the clay before modification, 28 parts by weight of the amine-based organic compound was used to modify clay.

Thereafter, the monomer composition was introduced through the feed section of a polymerization reactor consisting of continuously moving conveyer belt, and irradiated by UV through UV irradiation device (irradiation amount: 2 mW/cm$^2$) to progress UV polymerization for 2 minutes, thus preparing hydrogel polymer.

After transferring the hydrogel polymer to a cutter, it was cut to 0.2 cm.

Subsequently, the hydrogel polymer was dried in a hot air dryer of 185° C. for 40 minutes, and the dried hydrogel polymer was ground with a pin mill grinder. Thereafter, the ground hydrogel polymer was sieved with a standard sieve of ASTM standard to obtain polymer (base polymer powder) with a particle size (average particle diameter) of 150 μm to 850 μm.

Thereafter, based on 100 parts by weight of base polymer powder, cuprous oxide (Cupron A) of the contents described in the following Table 1, 0.2 parts by weight of EX-810 (epoxy crosslinking agent) as a surface crosslinking agent, 5 parts by weigh of water, and 3 parts by weight of methanol were mixed at 500 rpm for 30 seconds to form an antibacterial surface treatment solution. Such a surface treatment solution was sprayed onto the base polymer powder, stirred at room temperature, and mixed such that the surface treatment solution may be uniformly distributed on the base polymer powder. And then, the base polymer powder was put in a surface crosslinking reactor, and a surface crosslinking reaction was progressed.

Here, the surface-treated superabsorbent polymer was prepared by a heating reaction at 180° C. for 40 minutes. Specifically, in the surface crosslinking reactor, it was confirmed that the temperature of base polymer powder to which an antibacterial surface crosslinking solution was sprayed was gradually raised from the initial temperature of about 20° C., and it was operated such that the maximum reaction temperature of 180° C. was reached after 20 minutes. After reaching the maximum reaction temperature, the base polymer powder was additionally reacted for 40 minutes, and the finally prepared superabsorbent polymer sample was taken. After the surface crosslinking process, surface crosslinked superabsorbent polymer with a particle diameter of about 150 to 850 μm was obtained using a sieve.

Comparative Example 1

Superabsorbent polymer was prepared by the same method as Examples, except that cuprous oxide was not added to the surface crosslinking solution.

Comparative Examples 2 to 4

Superabsorbent polymer was prepared by the same method as Examples, except that cuprous acetate was added in the contents described in the following Table 1 to the surface crosslinking solution, instead of cuprous oxide.

Experimental Example 1

For the superabsorbent polymers of Examples 1 to 7 and Comparative Examples 1 to 4, properties such as CRC, AUP were measured and evaluated, and the measured property values were shown in the following Table 1. And, for the superabsorbent polymers of Examples 1 to 7 and Comparative Examples 1 to 3, properties such as vortex were measured and the results were shown in the following Table 2.

FIG. 1 compares and shows CRC and AUP according to the contents of cuprous oxide of Comparative Example 1, and Examples 1 to 7 according to one embodiment of the present invention.

TABLE 1

| Sample | | CRC (g/g) | AUP (g/g) | permeability |
|---|---|---|---|---|
| Example 1 | SAP + Cuprous oxide 0.025 phr | 36.4 | 22.8 | 755 s |
| Example 2 | SAP + Cuprous oxide 0.05 phr | 36.7 | 22.7 | 636 s |
| Example 3 | SAP + Cuprous oxide 0.1 phr | 37.6 | 22.2 | 796 s |
| Example 4 | SAP + Cuprous oxide 0.233 phr | 39.8 | 22.3 | — |
| Example 5 | SAP + Cuprous oxide 0.367 phr | 40.8 | 22.2 | — |
| Example 6 | SAP + Cuprous oxide 0.5 phr | 44.7 | 20.4 | 809 s |
| Example 7 | SAP + Cuprous oxide 1.0 phr | 45.1 | 17.9 | >1 h |
| Comparative Example 1 | SAP | 36.8 | 22.6 | 669 s |
| Comparative Example 2 | SAP + Cuprous Acetate 0.05 phr | 36.4 | 22.2 | 679 |
| Comparative Example 3 | SAP + Cuprous Acetate 0.5 phr | 39.5 | 20.3 | 836 |
| Comparative Example 4 | SAP + Cuprous Acetate 1.0 phr | 37.7 | 15.2 | |

TABLE 2

| | Vertex (s) | B.M. (%) | 16 h EC (%) | 1 h EC (%) | N.D. (%) | RM (ppm) |
|---|---|---|---|---|---|---|
| Example 1 | 44 | −29.6 | 24.8 | 10.1 | 79.5 | 402 |
| Example 2 | 43 | −31.5 | 24.1 | 10.6 | 79.8 | 389 |
| Example 3 | 42 | −27.9 | 26.9 | 10.7 | 79.8 | 318 |
| Example 6 | 46 | −26.0 | 40.9 | 15.7 | 80.8 | 260 |
| Example 7 | 43 | −27.0 | 45.9 | 17.9 | 81.8 | 139 |
| Comparative Example 1 | 45 | | | | | |
| Comparative Example 2 | 44 | | | | | |
| Comparative Example 3 | 46 | | | | | |

Referring to Tables 1 and 2, it was confirmed that, compared to Comparative Examples, the superabsorbent polymers of Examples 1 to 7 exhibit equivalent or more excellent absorption properties (CRC, AUP, etc.), and more improved antibacterial activities. And, as shown in FIG. 1, it can be seen that in the case of the superabsorbent polymers of Examples 1 to 7 wherein cuprous oxide was added during the surface crosslinking process, compared to Comparative Example 1 (cuprous oxide 0%), absorbency under pressure (AUP) is maintained or decreased a little, but centrifuge retention capacity (CRC) is significantly improved. Particularly, the superabsorbent polymer comprising 0.5 wt % of cuprous oxide of Example 6 exhibited excellent absorption properties of CRC 44 and AUP 20.

To the contrary, when progressing the experiments of Comparative Examples 2 to 4 using cuprous acetate, CRC increase according to the content was very small, and AUP decrease was remarkable. Due to such problems, the cuprous oxide of Comparative Examples 2 to 4 cannot be considered to be better than cuprous oxide of the present invention.

Examples 8 to 9

For the case wherein the surface crosslinking solution comprises cuprous oxide in the content of 0.001 parts by weight or more to 0.1 parts by weight, based on 100 parts by weight of the base polymer powder, experiments were progressed.

Namely, superabsorbent polymer was prepared by the same method as Example 1, except that the contents of cuprous oxide in the surface crosslinking solution were changed as described in Table 3.

Specifically, cuprous oxide (Cupron A) of the contents described in Table 3 (0.025 g(0.025 phr) or 0.05 g(0.05 phr)), 0.2 parts by weight of EX-810 (epoxy crosslinking agent) as a surface crosslinking agent, 5 parts by weight of water, and 3 parts by weight of methanol were mixed at 500 rpm for 30 seconds to form an antibacterial surface treatment solution. The surface treatment solution was sprayed to the base polymer powder, stirred at room temperature, and mixed such that the surface treatment solution may be uniformly distributed on the base polymer powder. And then, the base polymer powder was put in a surface crosslinking reactor and a surface crosslinking reaction was progressed.

After the surface crosslinking process, surface-crosslinked superabsorbent polymer with a particle diameter of about 150 to 850 μm was obtained using a sieve.

Comparative Example 5

Superabsorbent polymer was prepared by the same method as Example 1, except that cuprous oxide was not added to the surface crosslinking solution.

That is, based on 100 parts by weight of the base polymer powder, 0.2 parts by weight of EX-810 (epoxy crosslinking agent) as a surface crosslinking agent, 5 parts by weight of water, and 3 parts by weight of methanol were mixed at 500 rpm for 30 seconds, and then, crosslinking was progressed at 180° C. for 40 minutes.

Experimental Example 2

For the superabsorbent polymers of Examples 8 to 9 and Comparative Example 5, properties such as CRC, AUP were measured and evaluated, and the measured property values were shown in the following Table 3.

TABLE 3

| | Sample | CRC (g/g) | AUP (g/g) | permeability | Vertex (s) |
|---|---|---|---|---|---|
| Example 8 | SAP + Cuprous oxide 0.025 phr | 36.4 | 22.8 | 755 s | 44 |
| Example 9 | SAP + Cuprous oxide 0.05 phr | 36.7 | 22.7 | 636 s | 43 |
| Comparative Example 5 | SAP | 36.8 | 22.6 | 669 s | 45 |

Referring to Table 1, it can be seen that compared to Comparative Example 1, the superabsorbent polymers of Examples 8 to 9 exhibit equivalent or more excellent absorption properties (CRC, AUP, etc.).

Experimental Example 3

Bacterial Proliferation Inhibition Test

According to the antibacterial test method described in (11), comparative experiment of the bacterial proliferation inhibition effects of Comparative Example 5 and Examples 8 to 9 was progressed. The results were shown in FIG. 2 and Table 4. FIG. 2 compares and shows the antibacterial activity test result photographs of the superabsorbent polymers of Comparative Example 5 and Examples 8 to 9 according to one embodiment of the present invention.

TABLE 4

| | Bacteria concentration according to culture time(h) (CFU/mL) | | | | | | |
|---|---|---|---|---|---|---|---|
| | 0 h | 2 h | 4 h | 6 h | 8 h | 24 h | 24 h Antibacterial activity (%) |
| Comparative Example 5 | 16,000 | 13,200 | 14,900 | 12,300 | 12,300 | 24,300 | Standard |
| Example 8 | 15,200 | 9,100 | 700 | 500 | 2,000 | 1,000 | 99.96 |
| Example 9 | 15,200 | 6,800 | 600 | 200 | 200 | 600 | 99.98 |

As shown in Table 4 and FIG. 2, as the result of antibacterial test of Comparative Example 5 and Examples 8 to 9, bacterial proliferation increased in Comparative Example 5, compared to Example 8 to 9.

That is, in Comparative Example 5, $1.6 \times 10^3$ CFU/ml of bacteria increased to $2.43 \times 10^4$ CFU/ml, after 24 hours. However, in Examples 8 and 9 of the present invention, they decreased to $1.0 \times 10^3$ CFU/ml, and $6.0 \times 10^2$ CFU/ml, respectively, indicating that bacterial proliferation was inhibited compared to Comparative Example 5. It means that even if a very small amount (250 ppm or 500 ppm) of Cupron A is introduced, it inhibits bacterial proliferation 99.96%, and 96.98%, respectively.

In addition, it was confirmed that the superabsorbent polymer prepared by adding a specific antibacterial agent such as cuprous oxide during the surface crosslinking process of base polymer powder exhibits CRC, AUP, permeability, vortex values similar to Comparative Example without cuprous oxide (Cupron A 0%).

What is claimed is:

1. A method for preparing superabsorbent polymer comprising the steps of
   conducting crosslinking polymerization of water soluble ethylenically unsaturated monomers having acid groups of which at least a part are neutralized, in the presence of an internal crosslinking agent, to form hydrogel polymer;
   drying, grinding and sieving the hydrogel polymer to form base polymer powder; and
   surface crosslinking the base polymer powder using a surface crosslinking solution comprising a surface crosslinking agent and cuprous oxide as an antibacterial agent,
   wherein the cuprous oxide is included in the content of 0.001 to 2.5 parts by weight, based on 100 parts by weight of the base polymer powder.

2. The method according to claim 1, wherein the cuprous oxide is included in the content of 0.1 to 2.5 parts by weight, based on 100 parts by weight of the base polymer powder.

3. The method according to claim 2, wherein CRC is 39 to 50 g/g, and AUP is 16 to 23 g/g.

4. The method according to claim 1, wherein the cuprous oxide is included in the content of 0.001 to 0.1 parts by weight, based on 100 parts by weight of the base polymer powder.

5. The method according to claim 4, wherein CRC is 30 to 50 g/g, AUP is 16 to 25 g/g, and in antibacterial activity test using artificial urine containing $10^4$ CFU/ml of bacteria and nutrients, compared to superabsorbent polymer without cuprous oxide, at least 99% inhibition of bacterial proliferation is exhibited.

6. The method according to claim 1, wherein the cuprous oxide has a crystallite size of 20 to 55 nm, and an average particle diameter of 0.001 μm to 45 μm.

7. The method according to claim 1, wherein the surface crosslinking agent includes one or more selected from the group consisting of C3-20 polyhydric alcohol compounds, epoxy compounds, polyamine compounds, halo epoxy compounds and condensation products thereof, oxazoline-based compounds, mono-, di- and poly-oxazolidinone compounds, cyclic urea compounds, multivalent metal salts, and C2-5 alkylene carbonate compounds.

8. The method according to claim 1, wherein the step of surface crosslinking is conducted by a heating reaction at a temperature of 140 to 200° C. for 5 to 80 minutes.

9. The method according to claim 1, wherein the surface crosslinking solution further comprises water, methanol or a mixture thereof.

10. The method according to claim 1, wherein the water-soluble ethylenically unsaturated monomers include one or more selected from the group consisting of anionic monomers and salts thereof such as acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid or 2-(meth)acrylamide-2-methyl propane sulfonic acid; non-ionic hydrophilic group containing monomers such as (meth)acrylamide, N-substituted (meth)acrylate, 2-hydroxyethyl (meth)acrylate, 2-hydroxypropyl (meth)acrylate, methoxy polyethylene glycol (meth)acrylate, or polyethylene glycol (meth)acrylate; and amino group containing unsaturated monomers such as (N,N)-dimethylaminoethyl (meth)acrylate, (N,N)-dimethylaminopropyl (meth)acrylamide, and quarternarized products thereof.

11. The method for preparing superabsorbent polymer according to claim 1, wherein the internal crosslinking agent includes one or more selected from the group consisting of C8-12 bis(meth)acrylamide, poly(meth)acrylate of C2-10 polyol, and poly(meth)allylether of C2-10 polyol.

12. The method for preparing superabsorbent polymer according to claim 1, wherein the base polymer powder is ground and sieved to a particle diameter of 150 to 850 μm.

13. The method according to claim 1, wherein CRC is 44.7 g/g, and AUP is 20.4 g/g, when the cuprous oxide is included in the content of 0.5 parts by weight, based on 100 parts by weight of the base polymer powder, in the step of surface crosslinking.

14. Superabsorbent polymer comprising
base polymer powder comprising crosslinked polymer of water soluble ethylenically unsaturated monomers having acid groups of which at least a part are neutralized; and
a surface crosslink layer that is formed on the base polymer powder, and comprises cuprous oxide through a surface crosslinking agent,
wherein CRC is 39 to 50 g/g, and AUP is 16 to 23 g/g.

15. Superabsorbent polymer comprising
base polymer powder comprising crosslinked polymer of water soluble ethylenically unsaturated monomers having acid groups of which at least a part are neutralized; and
a surface crosslink layer that is formed on the base polymer powder, and comprises cuprous oxide through a surface crosslinking agent,
wherein CRC is 30 to 50 g/g, and AUP is 16 to 25 g/g, and in an antibacterial activity test using artificial urine containing $10^4$ CFU/ml of bacteria and nutrients, compared to superabsorbent polymer without cuprous oxide, at least 99% inhibition of bacterial proliferation is exhibited.

* * * * *